United States Patent
Epshteyn et al.

(10) Patent No.: US 10,081,649 B2
(45) Date of Patent: Sep. 25, 2018

(54) FIRST ROW TRANSITION METAL AMINO BOROHYDRIDES

(71) Applicant: The United States of America, as represented by the Secretary of the Navy, Washington, DC (US)

(72) Inventors: Albert Epshteyn, College Park, MD (US); Zachary J. Huba, Fort Lauderdale, FL (US); William Maza, Washington, DC (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/468,920

(22) Filed: Mar. 24, 2017

(65) Prior Publication Data
US 2017/0275320 A1    Sep. 28, 2017

Related U.S. Application Data

(60) Provisional application No. 62/313,357, filed on Mar. 25, 2016.

(51) Int. Cl.
| | |
|---|---|
| *C01B 6/23* | (2006.01) |
| *C07F 15/02* | (2006.01) |
| *C01B 3/00* | (2006.01) |
| *C01C 1/08* | (2006.01) |

(52) U.S. Cl.
CPC .......... *C07F 15/025* (2013.01); *C01B 3/0015* (2013.01); *C01B 6/23* (2013.01); *C01C 1/08* (2013.01); *Y02E 60/328* (2013.01); *Y02P 20/582* (2015.11)

(58) Field of Classification Search
CPC .............................. C07F 15/025; C01B 3/0015
USPC .............................................................. 568/8
See application file for complete search history.

(56) References Cited

U.S. PATENT DOCUMENTS

| | | |
|---|---|---|
| 6,651,701 B2 | 11/2003 | Kuriiwa et al. |
| 8,597,410 B2 | 12/2013 | Tung et al. |

FOREIGN PATENT DOCUMENTS

KR    10-2015-006326    6/2016

OTHER PUBLICATIONS

Ley et al., Materials Today 17(3), 2014, 122-128.*
Roedern et al., Inorg. Chem. 2015, 54, 10477-10482.*
Dionne et al., Can. J. Chem. 73: 1126-1134 (1995).*
Soloveichik, et al., Inorganic Chemistry 46 (10), 3790-3791 (2007).*
Soloveichik, et al., Inorg. Chem. 46 (10), 3790-3791 (2007). (Year: 2007).*
Dionne et al. "Preparation and characterization of a new series of Cr(II) hydroborates" Can. J. Chem. 73: 1126-1134 (1995).
Soloveichik et al. "Magnesium Borohydride Complexed by Tetramethylethylenediamine" Inorg. Chem. 2007, 46, 3790?3791.
International Search Report dated Jul. 4, 2017 in PCT/US/2017/024063.
Written Opinion of the International Searching Authority dated Jul. 4, 2017 in PCT/US/2017/024063.
Churchard, A. J. et al.. "Nickel macrocycles with complex hydrides: new avenues for hydrogen storage research," Energy & Environmental Science, 2010, vol. 3, No. 12, pp. 1973-1978.
Makhaev. V. D. et al., "Complex compounds of manganese (II) and zinc (II) tetrahydroborates with tetramethylethylenediamine" Russian journal of inorganic chemistry, 1995, vol. 40, No. 1, pp. 90-93.
Huba, Z. J. et al., "Investigating the decomposition pathways and hydrogen storage capacity of V, Cr, and Fe amino borohydrides" MRS Advances, 2016 [Epub. May 23, 20161. vol. 1, Issue. 42, pp. 2881-2886.
Tumanov, N. A. et al., "Challenges in the synthetic routes to Mn(BH4)2: insight into intermediate compounds" Dalton Transactions, 2015, vol. 44. No. 14, pp. 6571-6580.

* cited by examiner

*Primary Examiner* — Clinton A Brooks
*Assistant Examiner* — Kofi Adzamli
(74) *Attorney, Agent, or Firm* — US Naval Research Laboratory; Roy Roberts

(57) ABSTRACT

A transition metal amino borohydride material includes a first row transition metal in conjunction with an amine ligand and borohydride, in a condition of having been thermally treated to a temperature of at least 70° C. and up to but not including 800° C. An exemplary such material, $Fe(DETA)(BH_4)_2$ having been heat treated at 300° C., had good hydrogen storage characteristics.

9 Claims, 10 Drawing Sheets

101  102  103

FIRST ROW TRANSITION METAL AMINO BOROHYDRIDES

CROSS-REFERENCE TO RELATED APPLICATIONS

This Application claims the benefit of U.S. Provisional Application 62/313,357 filed on Mar. 25, 2016, the entirety of which is incorporated herein by reference.

BACKGROUND

Hydrogen ($H_2$) is an attractive energy carrier, with a combustion product that is primarily if not entirely water, and possesses high gravimetric energy density. However, it suffers from an extremely low volumetric energy density. Storing hydrogen under high pressures or in the liquid state can increase volumetric density, but storing hydrogen at high pressures or as a liquid requires expensive, specialized tanks that are expensive, inconvenient, and otherwise disadvantageous, especially in mobile applications. A need exists for materials that simultaneously possess stability, reversibility, and high usable hydrogen density.

BRIEF SUMMARY

The materials described herein are first row transition metal borohydride complexes with amino ligands that have been added to promote stability and increase $H_2$ content. The amino ligands can be in the form of small molecules, or they can be oligomeric, or polymeric in nature. The amino ligands impart stability on the metal borohydride complexes at room temperature, with thermal dehydrogenation occurring around 100° C., and gravimetric hydrogen densities between 5%-7.5%

In one embodiment, a transition metal amino borohydride material comprises a first row transition metal in conjunction with an amine ligand and borohydride, in a condition of having been thermally treated to a temperature from between at least 70° C. and up to but not including 800° C.

In a further embodiment, a method of making a transition metal amino borohydride material includes reacting a salt of a transition metal with a borohydride in a solvent, then adding an amine ligand to the solvent with mixing, then collecting a solid reaction product and heating to a temperature from between at least 70° C. and up to but not including 800° C., thereby obtaining transition metal amino borohydride material.

Another embodiment is a method of storing hydrogen by providing a transition metal amino borohydride material comprising a first row transition metal in conjunction with an amine ligand and borohydride, in a condition of having been thermally treated to a temperature from between at least 70° C. and up to but not including 800° C.; and introducing hydrogen into the material under elevated pressure, thereby causing hydrogen to be reversibly stored in the material.

BRIEF DESCRIPTION OF THE DRAWINGS

FIG. 6A: survey spectra, FIG. 6B: $Fe_{2p}$ spectra, FIG. 6C: $B_{1s}$ spectra, FIG. 6D: $N_{1s}$ spectra, FIG. 6E: $O_{1s}$ spectra, FIG. 6F: $Li_{1s}$ spectra, and FIG. 6G: $Cl_{2p}$ spectra.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

A new class of materials based on first row transition metal amino borohydride complexes is useful for hydrogen storage applications. The technique allows for high gravimetric and volumetric hydrogen density that can be released at relevant temperatures and pressures of technological interest. Identifying hydrogen storage materials that operate at relevant conditions and show reversibility is of importance due to the increasing need to use hydrogen as a fuel, particularly in mobility applications. This material represents a significant advance over currently known hydrogen storage technologies because it shows high hydrogen capacity that is reversible, while using low cost first row transition metals together with amino and borohydride ligands.

Metal borohydrides are made by dissolving a metal chloride in an appropriate solvent (for example, 1,2-dimethoxyethane, THF, etc.), then to that solvent adding an alkali metal borohydride complex (e.g., $NaBH_4$ and/or $LiBH_4$). The borohydride anions replace the chlorides on the metal, and in some cases reduce the metal center, resulting in a metal borohydride complex. The metal borohydride can then interact with the solvent molecules, stabilizing the metal borohydride. The preparation of transition metal amino borohydride complexes occurs by a similar method, but after the formation of the metal borohydride complex, a suitable amine ligand is added to react with the metal borohydride complex, replacing the stabilizing role of solvent molecules. The general preparation method is:

($M^1$=preferably $Cr^{3+}$, $V^{3+}$, or $Fe^{3+}$, but possibly any of the first row transition metals,) ($M^2$=Li or Na)

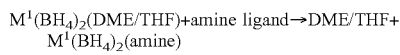

Figure 1:
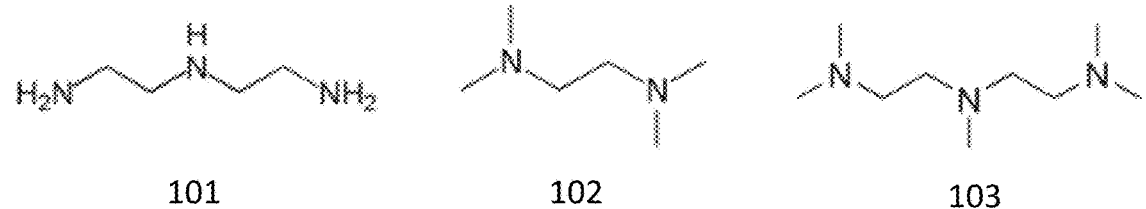
FIG. 1 shows amine ligands that have been used in preparing the first row transition metal borohydride complexes.

Examples of suitable amine ligands are shown in FIG. 1 and include diethylenetriamine (DETA) (101), tetramethylethylenediamine (TMEDA) (102), and/or pentamethyldiethylenetriamine (PMDETA) (103). A variety of other amine ligands could be used including those with longer chains and protonated and/or and permethylated varieties.

The process steps should be conducted under an inert atmosphere such as under nitrogen or argon gas.

EXAMPLES

Various complexes containing Cr, Fe, and V metal centers with varying amino ligands were prepared. Complexes containing the other first row transition metals, for example Ti, Co, Mn, Cu, Zn, are also envisioned.

Figure 2:
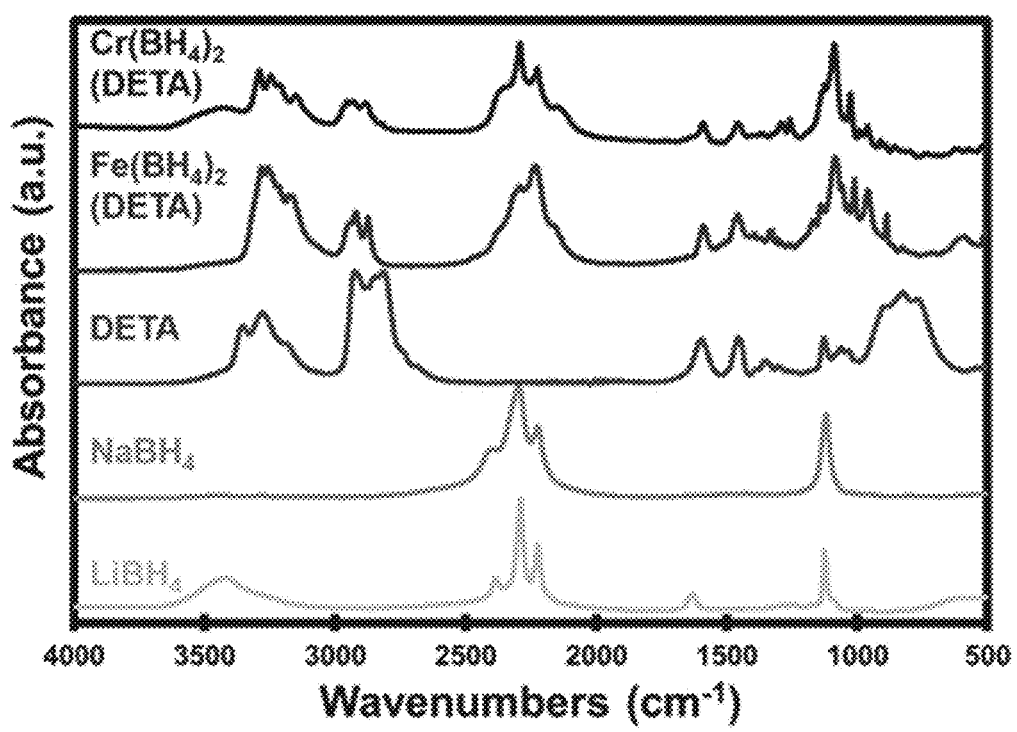
FIG. 2 shows Fourier transform infrared (FTIR) spectroscopy of prepared materials containing Fe and Cr.

FIG. 2 shows FT-IR spectra for synthesized Cr and Fe $(BH_4)_2$(DETA) complexes. These spectra were collected in a transmission geometry in a KBr pellet. The synthesized powders show characteristic absorbance at ≈2300 $cm^{-1}$, 3000 $cm^{-1}$, and 3200 $cm^{-1}$ corresponding to B—H, C—H, and N—H stretching modes, respectively. These absorbance bands are commensurate with those observed in corresponding precursors. However, it should be noted that the broad, free N—H band of the DETA at 800 $cm^{-1}$ is not observed in the synthesized complexes; implying that each amine moiety is ligated to the metal center, and minimal residual DETA precursor is present in the powders.

Figure 3A:
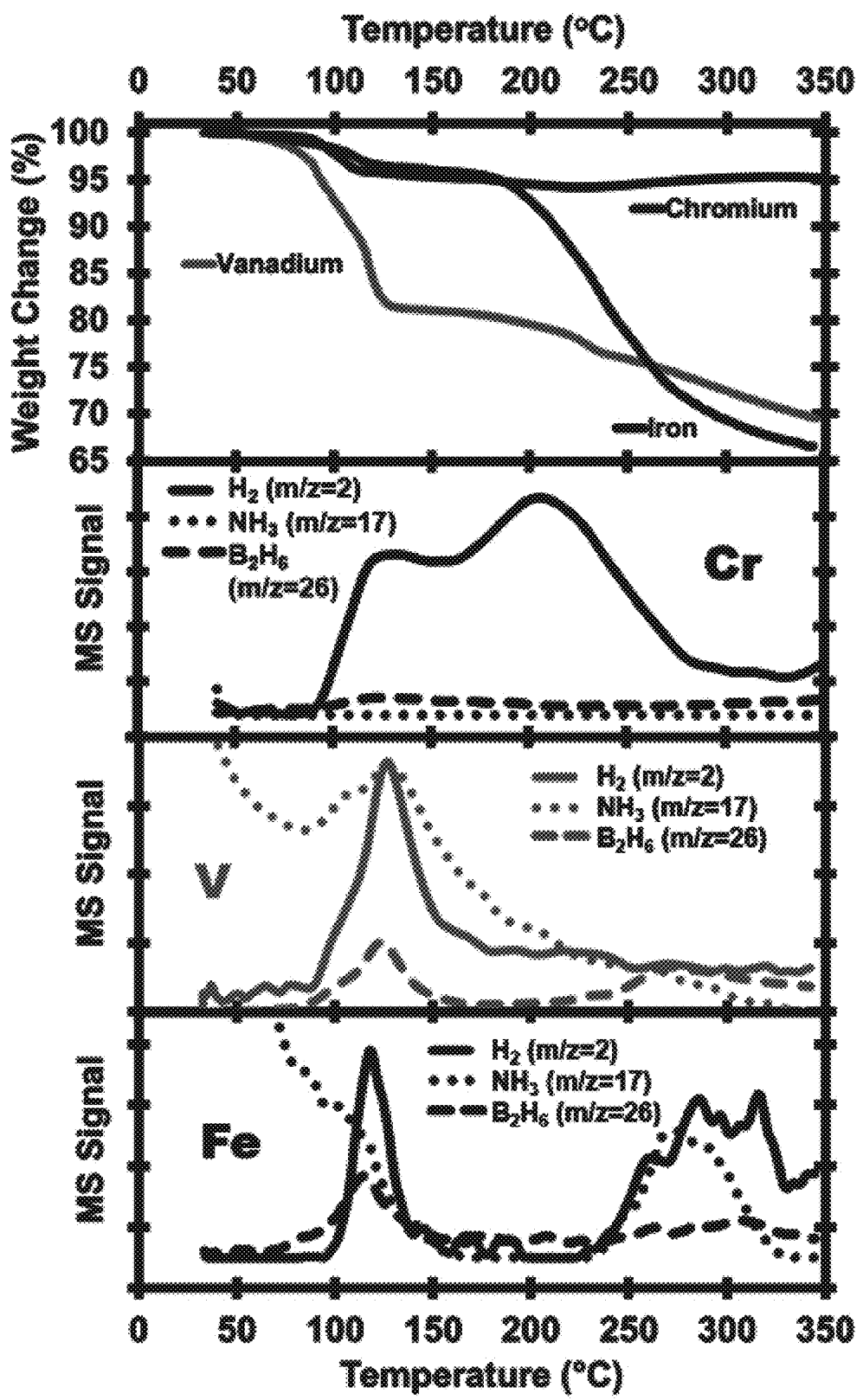
FIG. 3A shows thermogravimetric analysis (TGA) with mass spectrometry showing the decomposition behavior of prepared materials and their evolved gases upon decomposition.

FIG. 3A shows the TGA traces for the synthesized Cr, V, and Fe complexes with evolved gas analysis using a mass spectrometer attachment. The Cr complex showed a mass loss of 7.25%, with an onset temperature of 91.3° C. The evolved gas analysis showed only signal for $H_2$ (m/z=2) during this decomposition event. A 7.25% mass loss equates to a loss of 13 hydrogen atom equivalents per Cr complex molecule, which is the predicted number of H atoms on the B and N atoms per complex molecule.

The V amino borohydride complex lost 18.9% mass at 92.1° C., evolving $H_2$, $B_2H_6$ and $NH_3$ gases. This high degree of mass loss coupled with detection of $NH_3$ and $B_2H_6$ shows the V complex to have poor hydrogen release properties for a hydrogen storage material. Also, analysis of a product heated to 400° C. displayed a significant amount of residual B—H stretching modes in FT-IR, implying that very high temperatures are necessary to achieve complete dehydrogenation.

The Fe amino borohydride complex displayed bimodal decomposition behavior. At 94.8° C., a mass loss of 3.95% was recorded. The evolved gases were $H_2$ with a small signal for $B_2H_6$. Heating further to 196.8° C., resulted in a second mass loss event of 29.5% and release of $B_2H_6$ and $NH_3$ gases. The mass loss at 94.8° C., equates to the release of 7.5H atoms per Fe complex molecule.

Figure 3B:
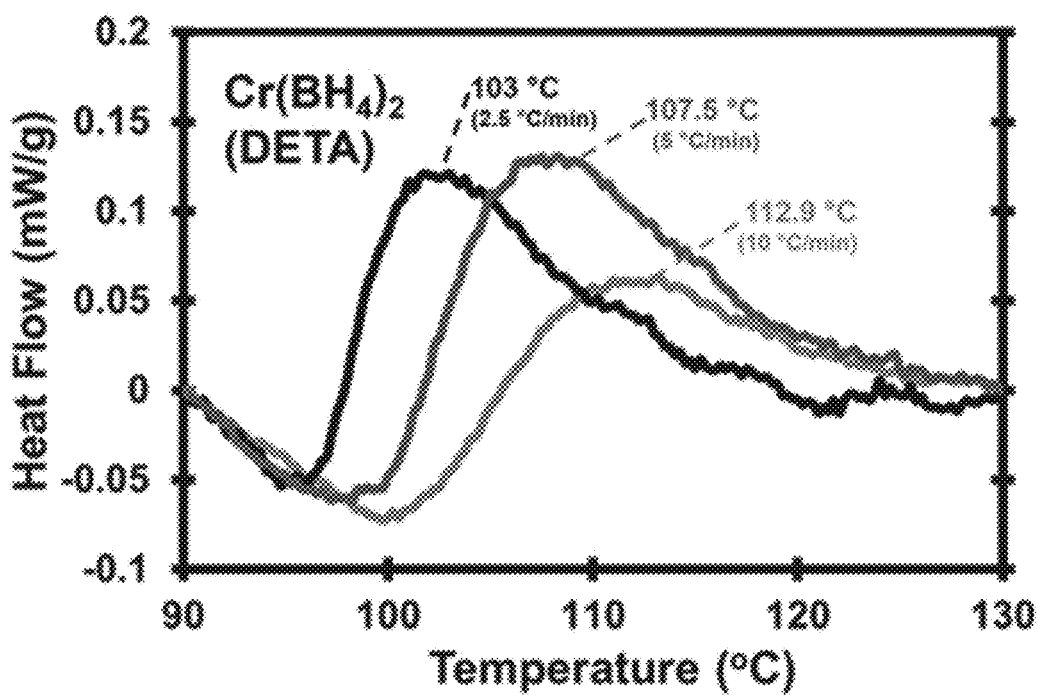
FIG. 3B shows differential scanning calorimetry (DSC) traces for the $Cr(BH_4)_2(DETA)$ complex at varying temperature ramp rates.
Figure 3C:
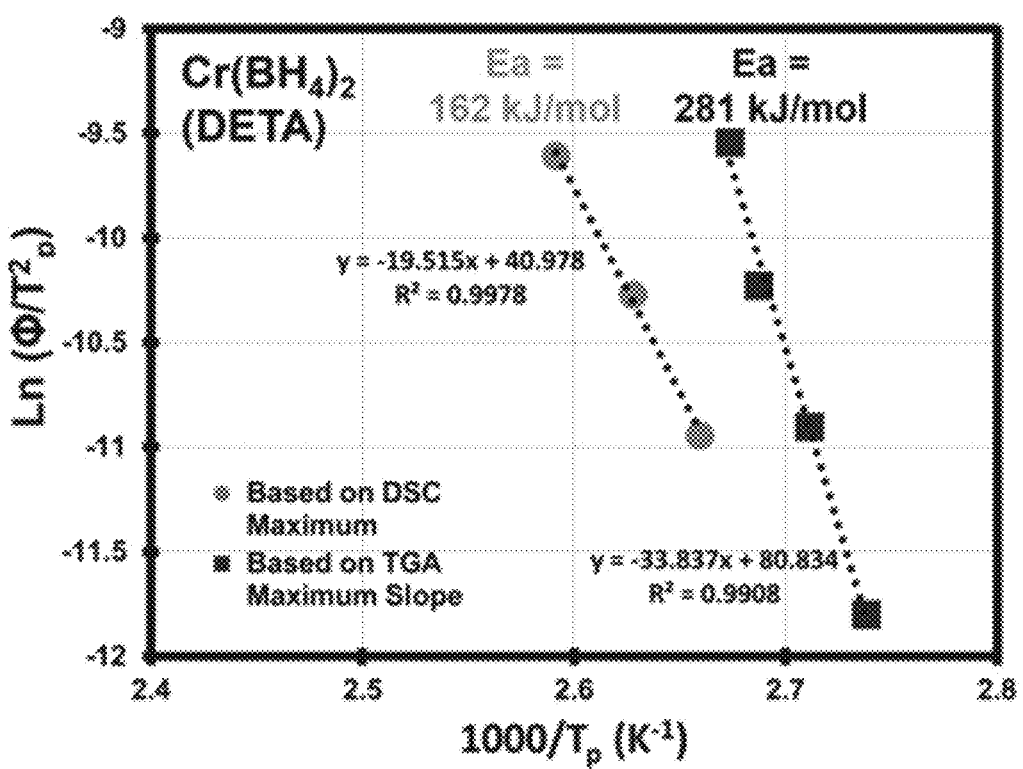
FIG. 3C is a Kissinger plot shown constructed from the data in FIG. 3C.

In order to assess the thermodynamic and kinetic aspects of decomposition, differential scanning calorimetry was used. FIG. 3B shows the calorimetry results during decomposition for $Cr(BH_4)_2$(DETA) at various heating rates. On average the decomposition process released 24 J/g, with peak heat release values between 103.0° C. and 112.9° C. for 2.5 and 10° C./min heating rates, respectively. Kissinger plots were constructed (FIG. 3C) using the observed peak temperature values and yielded an activation energy for decomposition of 162 kJ/mol. The activation energy calculated from simultaneous TGA measurements was calculated to be 281 kJ/mol. This discrepancy could be due to slowed detector response due to heat diffusion during the DSC collection. The Fe and V complexes were not analyzed using Kissinger analysis since their decomposition process was slower and occurred over a broad temperature range.

Figure 4A:
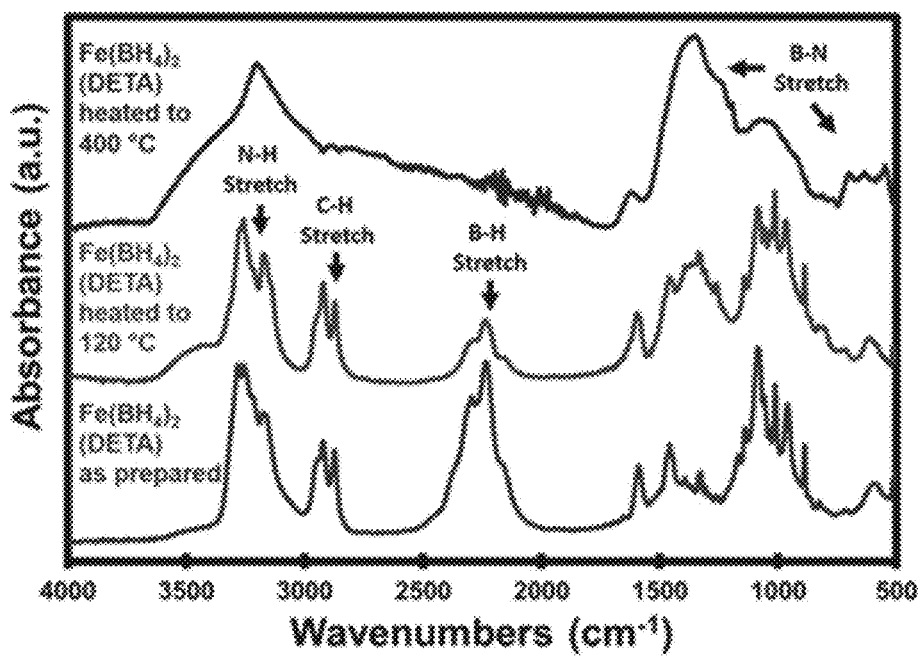
FIGS. 4A and 4B are FTIR spectra for Fe and Cr complexes, respectively, heated to varying temperatures.
Figure 4B:
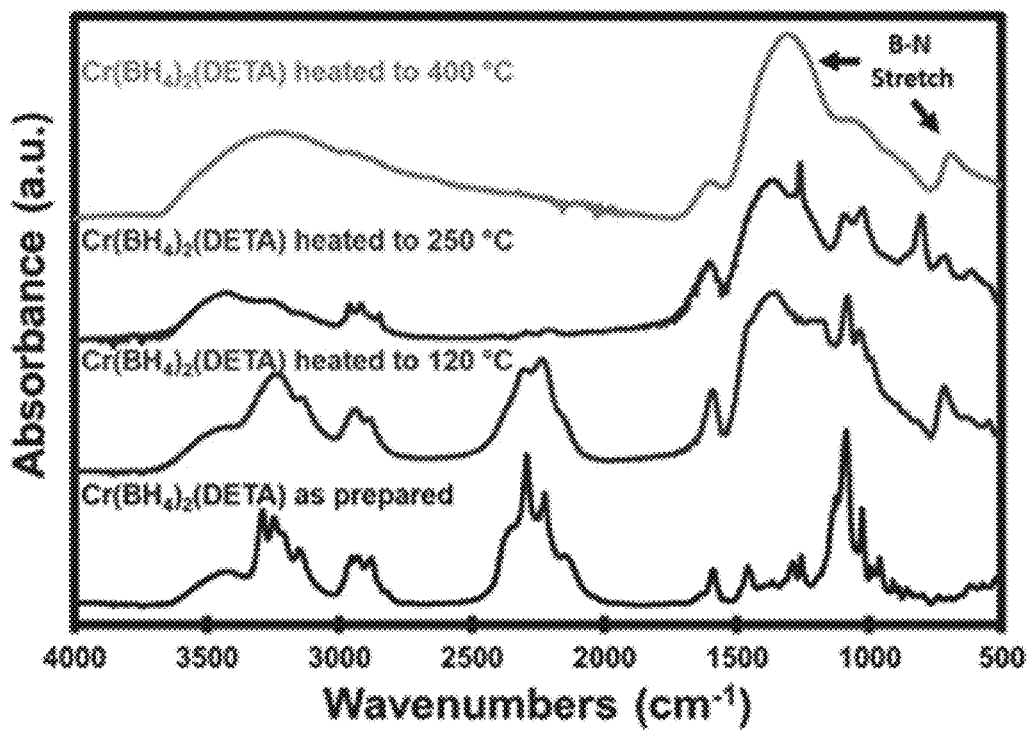

To further explore the decomposition behavior of metal amino borohydride complexes, intermediate decomposition products were analyzed using FTIR spectroscopy (FIGS. 4A and 4B). The Fe complex showed a decrease in B—H stretching mode signal when heated to 120° C. Heating to 400° C. results in a loss in B—H and C—H stretching modes and the emergence vibrational modes characteristic for boron nitride materials. N—H stretching modes were present for each Fe sample tested, but with diminished signal at higher temperatures. Upon heating the $Cr(BH_4)_2$(DETA) complex, a simultaneous loss in B—H and N—H absorbance is observed. At 120° C. this loss results in signal for a B—N stretching mode at ≈1400 $cm^{-1}$. At 250° C., minimal B—H and N—H absorbance is observed, with a significant decrease in C—H stretching signal. By 400° C. only signal for B—N vibrational modes are detected.

Thermalized Material

In a further example, amorphous Fe—N—B material was prepared by including a heat-treatment (thermalization) process and was found to exhibit good hydrogen storage ability. Synthetic procedures were conducted under inert conditions; that is, in a glovebox under an atmosphere of $N_2$. The material was prepared by first dissolving 5 g (31 mmol) of $FeCl_3$ in 500 mL dimethoxyethane (DME) producing a solution golden brown in color. This was added slowly to 2 g (93 mmol) $LiBH_4$ (also dissolved in DME) with vigorous stirring. The solution became lighter in color with a yellowish hue. This solution was allowed to stir at room temperature for one hour (or until the evolution of gas was observed to stop). Then around 4.5 g (4.3 mmol) of diethylenetriamine (DETA) was added dropwise to the solution and the resulting suspension was allowed to stir at room temperature for one hour. A dark red precipitate was observed to form initially upon addition of the DETA; this red precipitate, however, was observed to become yellowish (or tan in color when dry) over the course of the hour upon homogenization of the suspension with vigorous stirring. After the hour of stirring, the suspension was then filtered through a medium glass frit and the resultant tan colored powder was collected and dried by evacuation at room temperature under dynamic vacuum. A total of 5 g of product was recovered from filtration and evacuation. This product was then thermalized in a quartz vessel by heating to 350° C. and 800° C. over a sand bath or furnace, respectively, under dynamic vacuum.

Figure 5A:
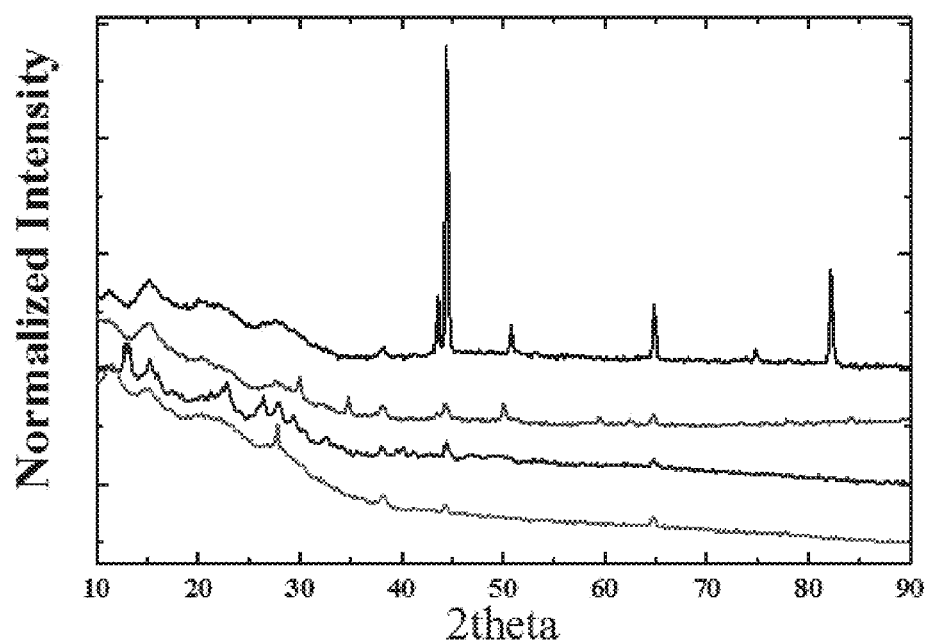
FIG. 5A shows X-ray powder diffraction patterns: the lower line is background, the second line from the bottom is as-synthesized $Fe(DETA)(BH_4)_2$, the third line from the bottom is the same heated to 350° C., and the top line is the same heated to 800° C.
Figure 5B:
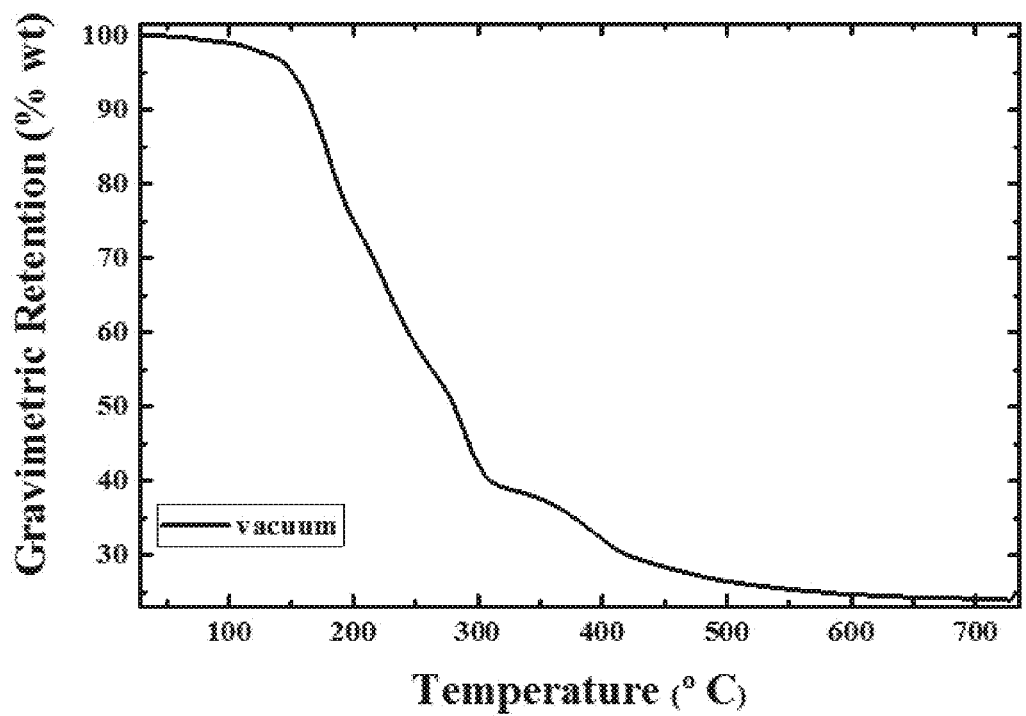
FIG. 5B shows thermal gravimetric analyses of $Fe(DETA)(BH_4)_2$ under vacuum.
Figure 5C:
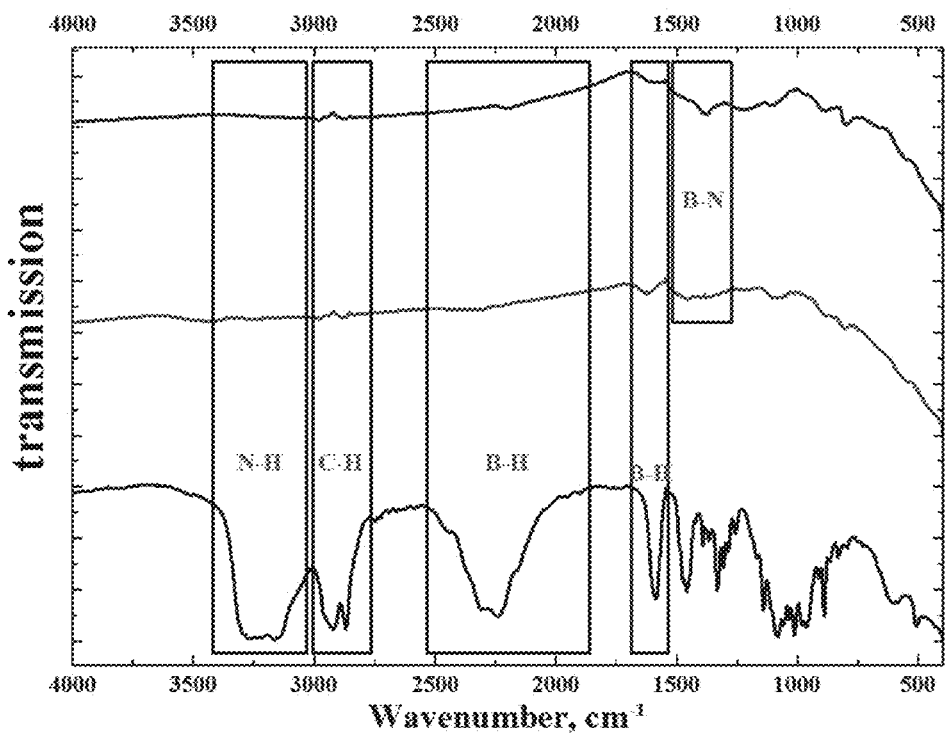
FIG. 5C is an FTIR spectra of a $Fe(DETA)(BH_4)_2$ sample as synthesized (bottom line), heated to 350° C. (middle line), and 800° C. (top).
Figure 5D:
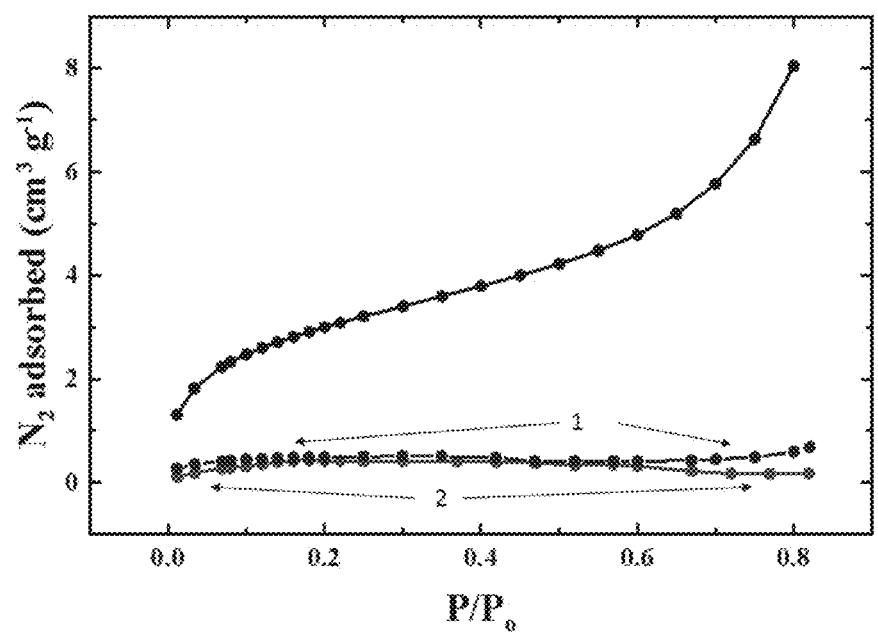
FIG. 5D is a nitrogen adsorption isotherms for $Fe(DETA)(BH_4)_2$ with no treatment (top line), the same heated to 350° C. (labeled 2), 800° C. (labeled 1).
Figure 6A:
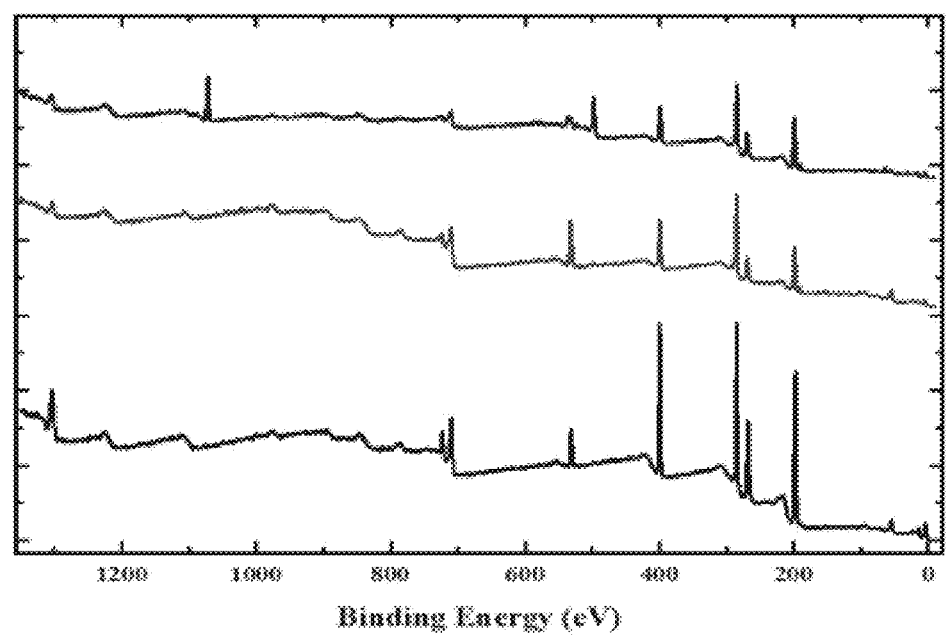
FIGS. 6A-G show X-ray photoelectron spectra of $Fe(DETA)(BH_4)_2$ as synthesized (bottom line), heated to 350° C. (middle line), and 800° C. (top line).
Figure 6B:
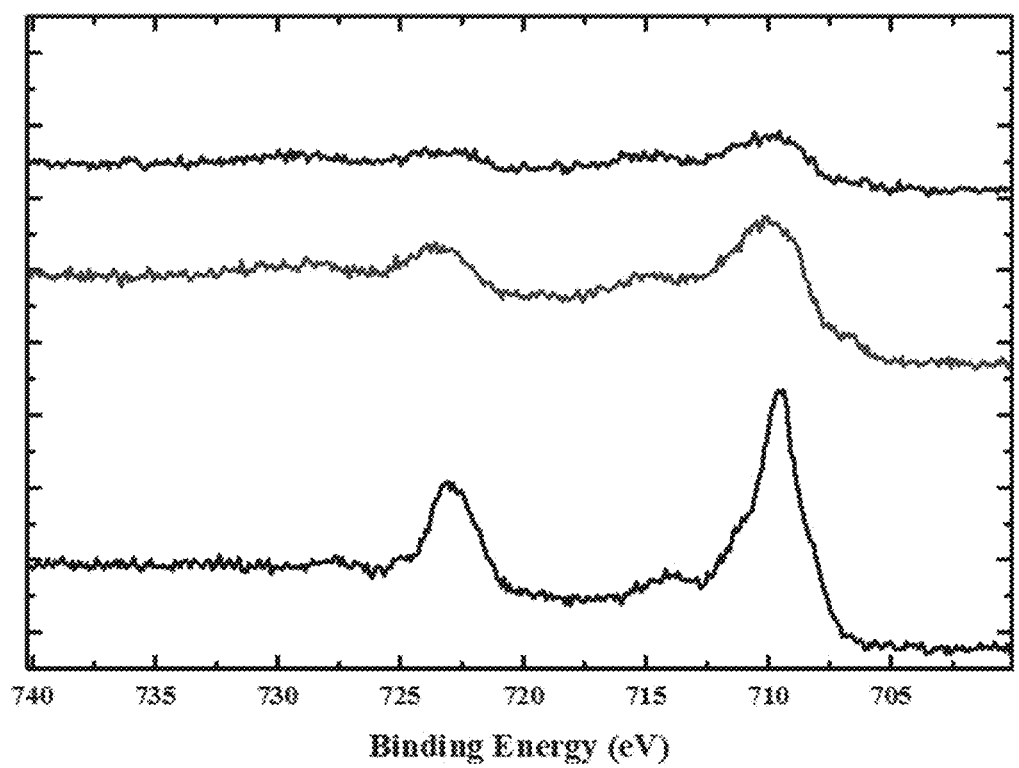
Figure 6C:
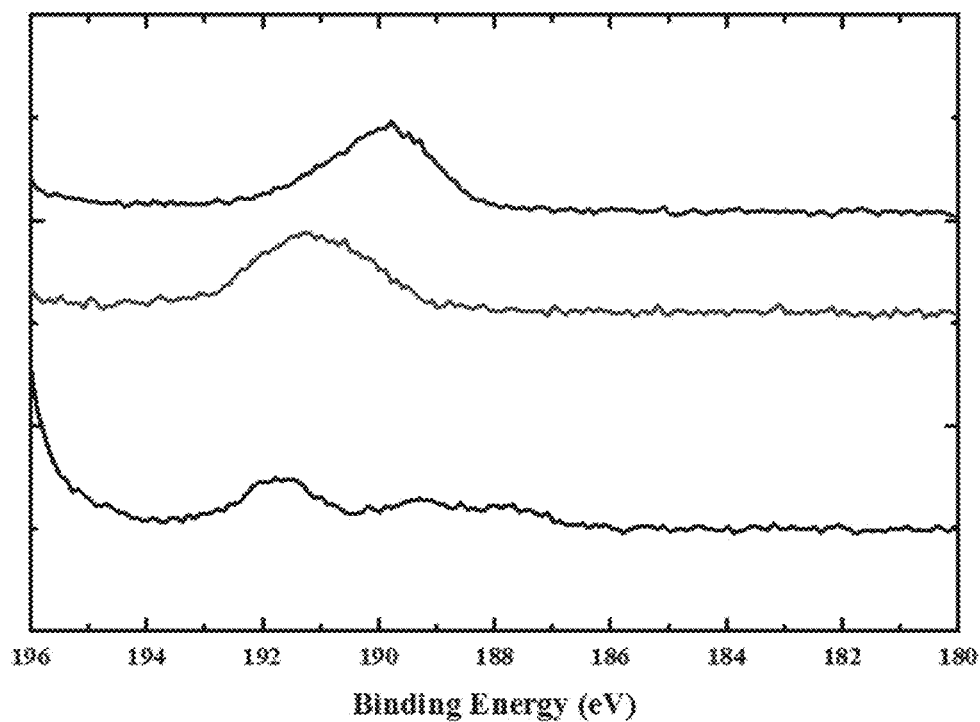
Figure 6D:
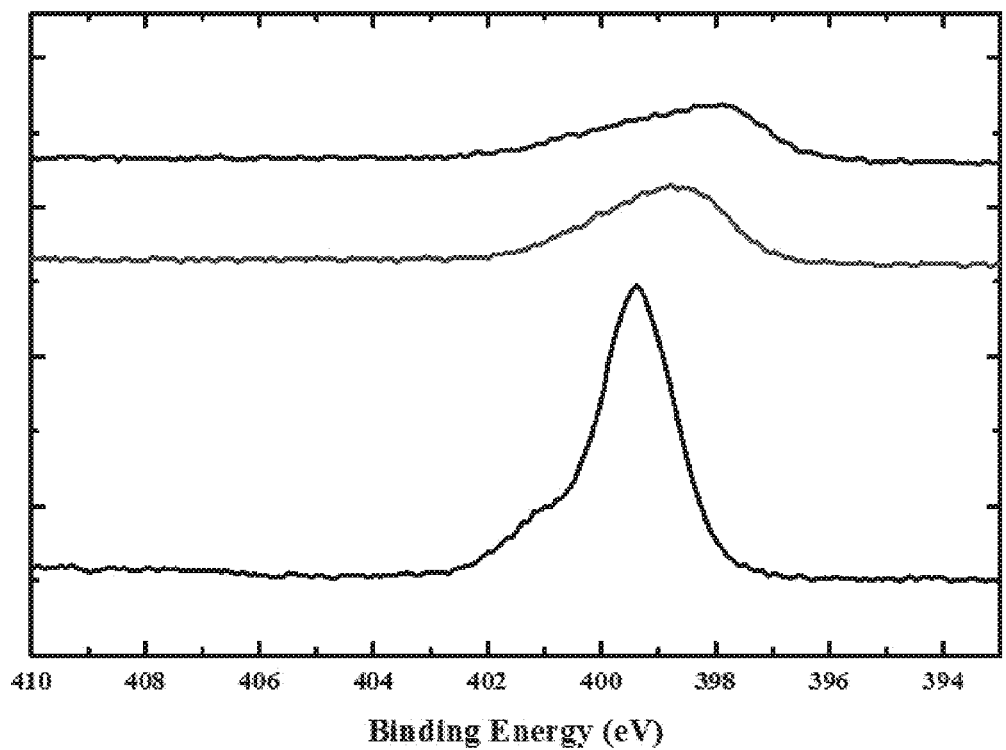
Figure 6E:
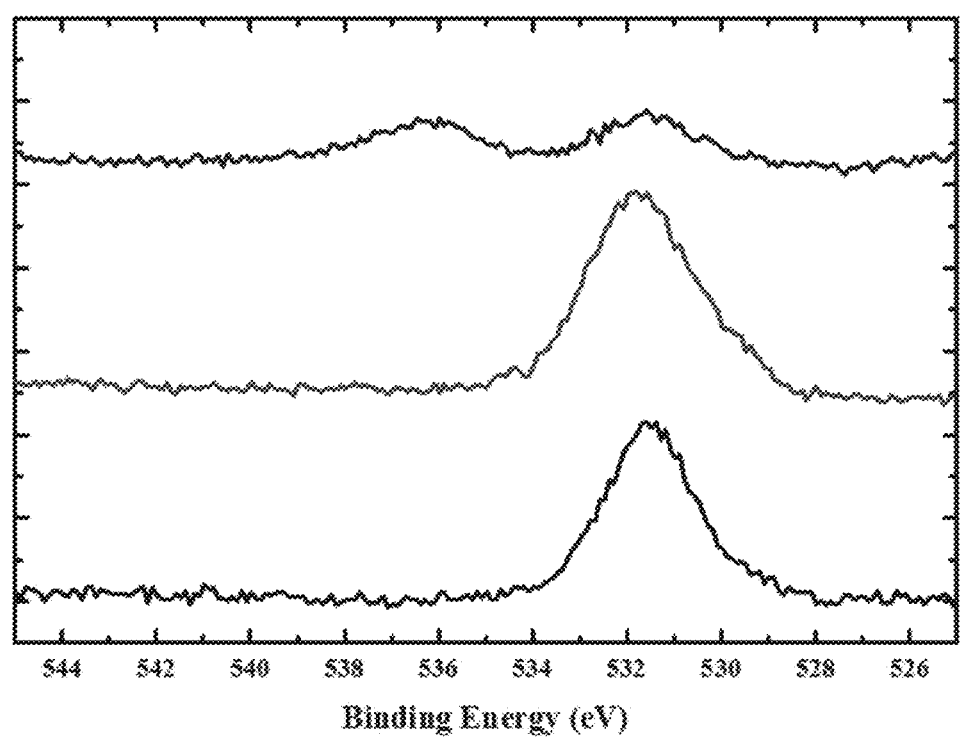
Figure 6F:
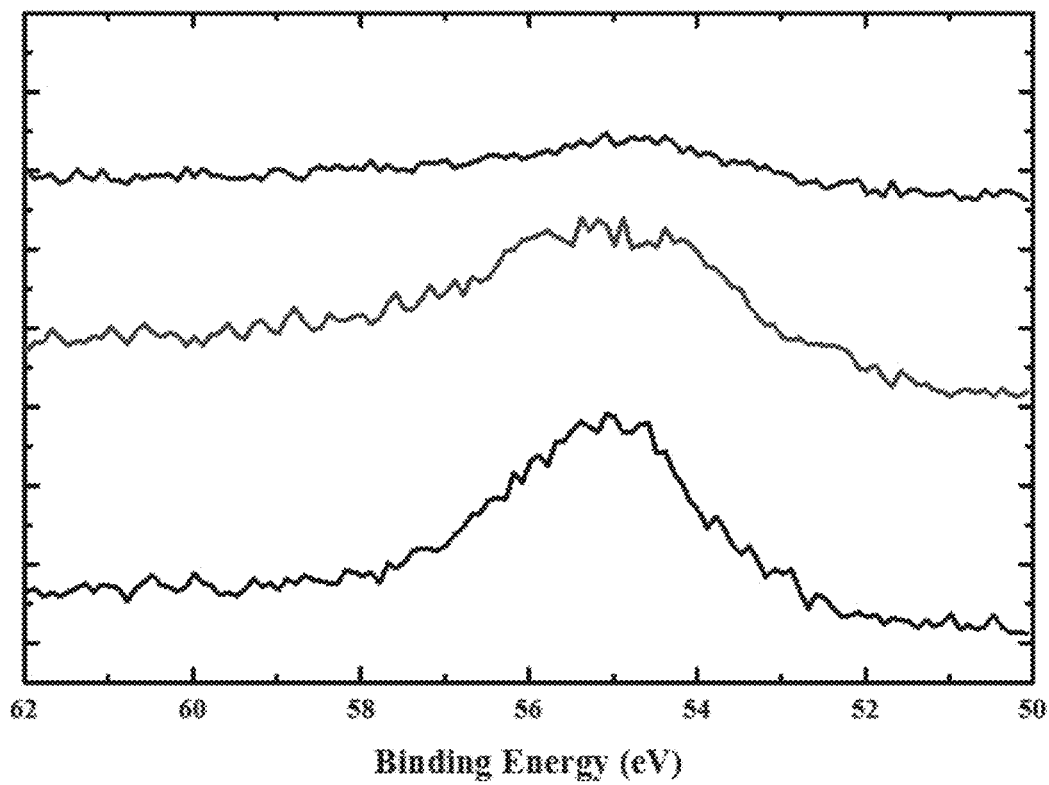
Figure 6G:
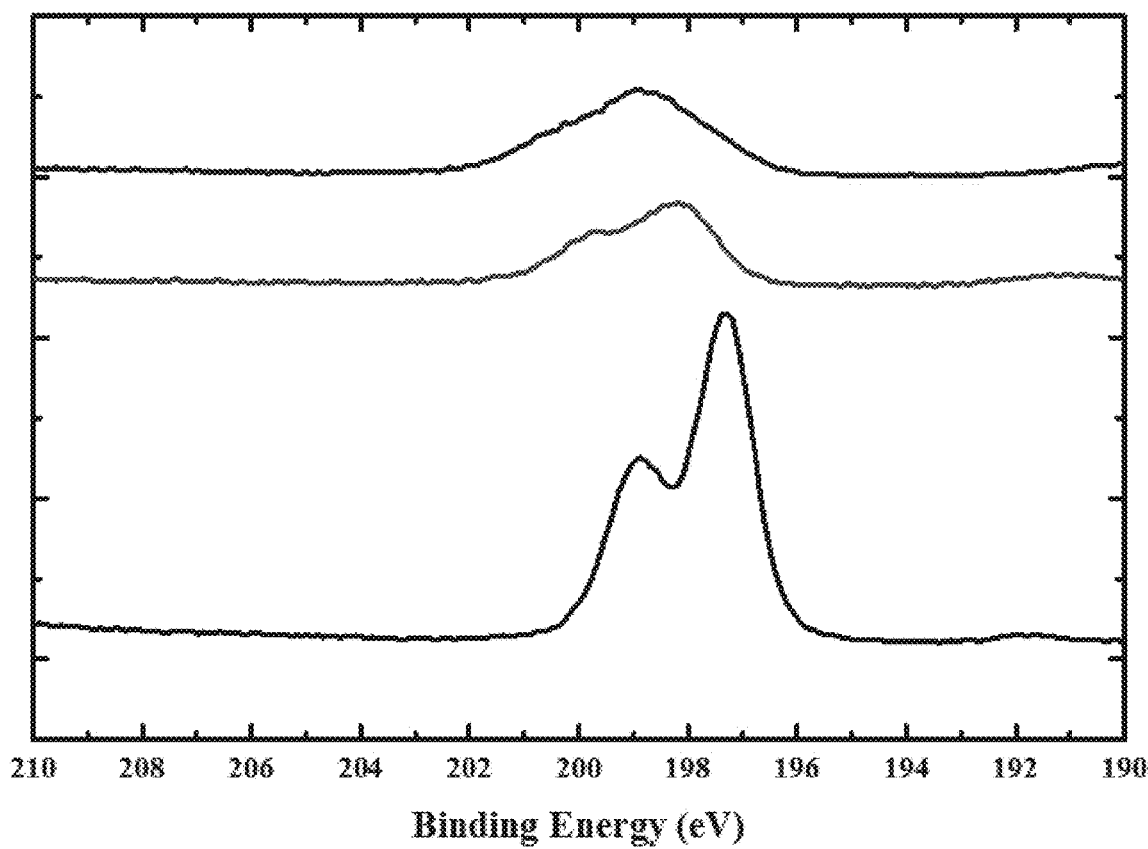

The addition of DETA to a DME solution of $Fe(BH_4)_2$ resulted in a pale yellowish tan amorphous solid product as evidenced by powder X-ray diffraction (PXRD) which is relatively featureless up to 800° C. (FIG. 5A). After heating to 800° C. the PXRD pattern displays signals located at 2Θ of 43.6°, 44.4°, 50.8°, 64.8°, and 82.2°. These neither match the background signal, nor the Pnma, P63mc, Ama2, and Fm3m known crystallographic forms of $LiBH_4$. Thermogravimetric analysis of $Fe(DETA)(BH_4)_2$ under vacuum displays an approximately 60% loss of mass between 150° C. and 300° C. (FIG. 5B) which is in good agreement with a previous reported result which was attributed to the evolution of $H_2$, $B_2H_6$, and $NH_3$. Upon evacuation, the FTIR spectra of the $Fe(DETA)(BH_4)_2$ displays (FIG. 5C) characteristic signals between 1500 $cm^{-1}$ and 1650 $cm^{-1}$ as well as between 2000 $cm^{-1}$ and 2500 $cm^{-1}$ corresponding to B—H bending and stretching modes, respectively. Signals corresponding to C—H and N—H stretching modes are also present between 2700 $cm^{-1}$-3000 $cm^{-1}$ and 3000 $cm^{-1}$-3400 $cm^{-1}$. Upon heating the material to 350° C. for 8 hours these features are no longer present in the FTIR spectra. When heated to 800° C. a weak signal is observed at 1390 $cm^{-1}$ that may be due to the formation of B—N bonds.

X-ray photoelectron spectra of the un-treated material display relatively strong signals at 709.6 eV and 723.1 eV and much weaker signals at 714.1 eV and 727.6 eV corresponding to Fe $2p_{3/2}$ (low energy) and $2p_{1/2}$ (high energy) electrons, respectively. The $2p_{3/2}$ signals are distinct from those observed for $FeCl_3$ which appears at 711.5 eV and closer to those observed for $FeCl_2$ at 710.8 eV potentially confirming the oxidation state of the Fe as in the ferrous form. The position of the Fe 2p signals displayed no significant shifts upon heating the material to 350° C. and 800° C. indicating no change in the oxidation state of the Fe with heat treatment. The Fe $2p_{3/2}$ signal observed at 714.1 eV resembles that observed for ferric $FeF_3$ at 714.4 eV suggesting the potential presence of a second ferric iron species. The B 1s spectra of the untreated sample displays multiple signals at 187.8 eV, 189.5 eV, and 191.7 eV; upon heating to 350° C. a single band is observed at 191.3 eV and 189.8 eV upon heating to 800° C. The N 1s signal of the untreated and treated material shows two overlapping bands upon analysis—a relatively strong band centered at 399.4 eV and another weaker signal at 401.1 eV for the untreated sample. The later band displays a shift to 398.4 eV upon heating to 350° C. and 397.8 eV when heated to 800° C. The photoelectron spectra of the untreated and heated materials also display bands corresponding to O 1s, Li 1s, Cl 2p atoms. No significant changes in the band position are observed for the Li 1s signal at 55.2 eV upon heating the material to 800° C. Similarly, the position of the O 1s band is centered at around 531.5 eV up to 350° C.; at 800° C. a second band centered at 536.3 eV is observed in addition to the primary band at 531.5 eV. The Cl $2p_{3/2}$ is observed to shift from 197.3 eV (for the untreated sample) to 198.0 eV when heated to 350° C. and 198.8 eV when heated to 800° C.

Brunauer-Emmett-Teller (BET) analysis of the $Fe(DETA)(BH_4)_2$ compound indicates a surface area of approximately 12 $m^2/g$ which decreases significantly to approximately 2 $m^2/g$ upon heating to 350° C. with little additional change upon heating to 800° C. (Table 1). Despite the low surface area obtained by BET analysis, the material demonstrates a gravimetric capacity for $H_2$ sorption of approximately 1% by wt at 70 atm and −150° C. which is comparable to $H_2$ sorption by the high surface area (555 $m^2/g$) porous metal-organic framework UiO-66 (Table 1).

TABLE 1

| Material | BET surface area ($m^2$ $g^{-1}$) | % $H_2$ mass uptake (70 atm, 123K) |
| --- | --- | --- |
| $Fe(DETA)(BH_4)_2$ | 11.6 ± 0.1 | 0.74% wt |
| FeNB that had been heated to 350° C. | 1.39 ± 0.10 | 0.99% wt |
| FeNB that had been heated to 800° C. | 1.58 ± 0.05 | 0.31% wt |
| UiO-66 | 556 ± 16 (823[†]) | 1.02% wt (2.6% wt at 77K, 26 atm[†]) |

It is expected that the favorable impact of thermal treatment below 800° C. will extend to other first row transition metal amino borohydride complexes including those with other transition metals and those incorporating other ligands. Such materials might be thermally treated for a period of time ranging from one hour up to several days, at a temperature ranging from 70° C. and up to but not including 800° C.

Further Envisioned Embodiments

Also contemplated are devices for hydrogen storage and method for using such devices. The devices can include a transition metal amino borohydride complex enclosed in a suitable vessel (e.g., one capable of withstanding the associated pressures) with at least one port for inlet and outlet of hydrogen gas. A device optionally further includes heating and/or cooling mechanisms. A method of using the device can include loading hydrogen into it and causing the hydrogen to be released from it simply by regulating the temperature and pressure of hydrogen within the said vessel. It would be relatively facile to design such a vessel/system to take on any size and/or shape, as the associated temperatures of <200° C., and pressures <100 bar (optionally plus a safety factor of 50% or greater) are easily containable using available technology.

Suitable hydrogen-storage devices designed for use with metal hydrides are known in the art, for example as described in U.S. Pat. Nos. 8,597,410 and 6,651,701, each incorporated herein by reference for the disclosure of such devices and methods of their use. They could be adopted for use with the transition metal amino borohydride complexes described herein.

Advantages

The technique described herein allows for high gravimetric and volumetric hydrogen densities, as well as efficient hydrogen release and uptake at moderate temperature and hydrogen pressure. Additional desired properties include the use of inexpensive starting materials and hydrogen recyclability. The material described in this disclosure uses earth abundant first row transition metals, boron and nitrogen, indicating that they will be more affordable to produce than competing materials such as metal-organic frameworks.

CONCLUDING REMARKS

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

What is claimed is:

1. A transition metal amino borohydride material comprising:
   a first row transition metal in conjunction with a polymeric amine ligand having at least three amine groups and borohydride, in a condition of having been thermally treated to a temperature of 70° C. or greater and less than 800° C.

2. The material of claim 1, wherein said material is amorphous.

3. The material of claim 1, wherein said first row transition metal is selected from the group consisting of $Cr^{3+}$, $V^{3+}$, and $Fe^{3+}$.

4. The material of claim 1, wherein said amine ligand is diethylenetriamine.

5. The material of claim 1, wherein said a first row transition metal in conjunction with an amine ligand and borohydride is $Fe(DETA)(BH_4)_2$.

6. The material of claim 1, wherein said thermal treatment has been made at a temperature of 350° C. or greater.

7. A transition metal amino borohydride material comprising:
   chromium in conjunction with a polymeric amine ligand having at least three amine groups and borohydride, in a condition of having been thermally treated to a temperature of 70° C. or greater and less than 800° C.

8. A transition metal amino borohydride material comprising:
   a first row transition metal in conjunction with a diethylenetriamine ligand and borohydride, in a condition of having been thermally treated to a temperature of 70° C. or greater and less than 800° C., wherein the material is polymeric.

9. The material of claim 8, wherein the metal is chromium.

* * * * *